(12) United States Patent
Zucker (10) Patent No.: US 7,008,441 B2
(45) Date of Patent: Mar. 7, 2006

(54) BALLOON METHOD AND APPARATUS FOR VASCULAR CLOSURE FOLLOWING ARTERIAL CATHETERIZATION

(75) Inventor: Menachem Zucker, Kiryat Motzkin (IL)

(73) Assignee: Cardiodex, Tirat-Hacarmel (IL)

( * ) Notice: Subject to any disclaimer, the term of this patent is extended or adjusted under 35 U.S.C. 154(b) by 282 days.

(21) Appl. No.: 10/288,843

(22) Filed: Nov. 6, 2002

(65) Prior Publication Data

US 2003/0055454 A1 Mar. 20, 2003

Related U.S. Application Data

(62) Division of application No. 09/808,630, filed on Mar. 14, 2001, now Pat. No. 6,743,195.

(51) Int. Cl.
*A61B 17/08* (2006.01)

(52) U.S. Cl. .................................................. 606/213
(58) Field of Classification Search ................ 606/213
See application file for complete search history.

(56) References Cited

U.S. PATENT DOCUMENTS

| | | | |
|---|---|---|---|
| 1,881,250 A | 10/1932 | Tomlinson | |
| 3,595,238 A | 7/1971 | Gavrilov et al. | |
| 3,886,944 A | 6/1975 | Jamshidi | |
| 4,202,337 A | 5/1980 | Hren et al. | |
| 4,364,392 A | 12/1982 | Strother et al. | 128/325 |
| 4,539,987 A | 9/1985 | Nath et al. | |
| 4,744,364 A | 5/1988 | Kensey | 128/334 |
| 4,836,204 A | 6/1989 | Landymore et al. | 128/334 |
| 4,929,246 A | 5/1990 | Sinofsky | |
| 5,103,804 A | 4/1992 | Abele et al. | |
| 5,122,137 A | 6/1992 | Lennox | |
| 5,211,624 A | 5/1993 | Cinberg et al. | |
| 5,217,024 A | 6/1993 | Dorsey et al. | 128/758 |
| 5,342,393 A | 8/1994 | Stack | |
| 5,349,166 A | 9/1994 | Taylor | |
| 5,370,660 A | 12/1994 | Weinstein et al. | 606/215 |
| 5,413,571 A | 5/1995 | Katsaros et al. | 606/213 |
| 5,415,657 A | 5/1995 | Taymor-Luria | |
| 5,419,765 A | 5/1995 | Weldon et al. | 604/96 |
| 5,486,195 A | 1/1996 | Myers et al. | 606/213 |
| 5,507,744 A | 4/1996 | Tay et al. | |
| 5,540,715 A | 7/1996 | Katsaros et al. | 606/213 |
| 5,626,601 A | 5/1997 | Gershony et al. | |
| 5,645,566 A | 7/1997 | Brenneman et al. | 606/213 |
| 5,700,277 A | 12/1997 | Nash et al. | 606/213 |
| 5,716,375 A | 2/1998 | Fowler | |
| RE35,755 E | 3/1998 | Qian | |

(Continued)

FOREIGN PATENT DOCUMENTS

WO WO-94/24948 11/1993

(Continued)

OTHER PUBLICATIONS

Overview of Compressar. 2002.

(Continued)

*Primary Examiner*—Gary Jackson
(74) *Attorney, Agent, or Firm*—Patton Boggs LLP (57) ABSTRACT

Apparatus for hemostasis of an artery having a puncture after arterial catheterization, the apparatus includes a catheter introducer having a forward end and a hemostasis device including an elongate flexible hollow shaft having an inflatable anchor balloon at a forward end thereof and an inflatable peripheral balloon adjacent the forward end of the flexible hollow shaft, the hemostasis device being arranged to be insertable into an artery via the catheter introducer.

A method for hemostasis of an artery having a puncture after arterial catheterization is also disclosed.

3 Claims, 13 Drawing Sheets

U.S. PATENT DOCUMENTS

| | | | |
|---|---|---|---|
| 5,725,551 A | 3/1998 | Myers et al. | 606/213 |
| 5,728,133 A | 3/1998 | Kontos | |
| 5,728,134 A | 3/1998 | Barak | 606/214 |
| 5,782,860 A | 7/1998 | Epstein et al. | |
| 5,810,810 A | 9/1998 | Tay et al. | |
| 5,853,421 A | 12/1998 | Leschinsky et al. | 606/213 |
| 5,868,778 A | 2/1999 | Gershony et al. | |
| 5,879,499 A | 3/1999 | Corvi | 156/175 |
| 5,891,138 A | 4/1999 | Tu et al. | |
| 5,895,386 A | 4/1999 | Odell et al. | |
| 5,922,009 A | 7/1999 | Epstein et al. | |
| 5,928,266 A | 7/1999 | Kontus | 606/213 |
| 5,941,897 A | 8/1999 | Myers | |
| 6,033,401 A | 3/2000 | Edwards et al. | |
| 6,048,358 A | 4/2000 | Barak | 606/213 |
| 6,056,768 A | 5/2000 | Cates et al. | |
| 6,063,085 A | 5/2000 | Tay et al. | |
| 6,113,598 A | 9/2000 | Baker | |
| 6,142,994 A | 11/2000 | Swanson et al. | |
| 6,152,920 A | 11/2000 | Thompson et al. | |
| 6,228,082 B1 | 5/2001 | Baker et al. | |
| 6,235,027 B1 | 5/2001 | Herzon | |
| 6,352,533 B1 | 3/2002 | Ellman et al. | |
| 6,398,782 B1 | 6/2002 | Pecor et al. | |
| 6,443,947 B1 | 9/2002 | Marko et al. | |
| 6,468,272 B1 | 10/2002 | Koblish et al. | |
| 6,529,756 B1 | 3/2003 | Phan et al. | |
| 6,533,778 B1 | 3/2003 | Herzon | |
| 6,551,313 B1 | 4/2003 | Levin | |
| 6,569,161 B1 | 5/2003 | Zappala | |
| 6,656,136 B1 | 12/2003 | Weng et al. | |
| 6,676,685 B1 | 1/2004 | Pedros et al. | |
| 6,904,303 B1 | 6/2005 | Phan et al. | |
| 2001/0029373 A1 | 10/2001 | Baker et al. | |
| 2002/0156495 A1 | 10/2002 | Brenneman et al. | |
| 2002/0193808 A1 | 12/2002 | Belef et al. | |
| 2003/0093116 A1 | 5/2003 | Nowakowski | |
| 2003/0125766 A1 | 7/2003 | Ding | |
| 2003/0199863 A1 | 10/2003 | Swanson et al. | |
| 2003/0236518 A1 | 12/2003 | Marchitto et al. | |
| 2004/0249342 A1 | 12/2004 | Khosravi et al. | |

FOREIGN PATENT DOCUMENTS

| | | |
|---|---|---|
| WO | WO-93/21844 | 11/1994 |
| WO | WO9811830 | 3/1998 |

OTHER PUBLICATIONS

ANGIO-SEAL™111. 2002.

The PROSTAR®, Perclose, Inc. 2002.

Silber, S. "Vascular Closure Devices for Immediate . . . " In Handbook of Coronary Stents, $3^{RD}$ Ed. (Martin Dunitz, 2000).

BALLOON METHOD AND APPARATUS FOR VASCULAR CLOSURE FOLLOWING ARTERIAL CATHETERIZATION

This application is a division of application Ser. No. 09/808,630, filed Mar. 14, 2001, now U.S. Pat. No. 6,743,195.

FIELD OF THE INVENTION

The present invention relates to catheterization systems and methodologies generally and more particularly to post-catheterization closure.

BACKGROUND OF THE INVENTION

Applicant's U.S. Pat. No. 5,728,134 and Published PCT Patent application WO 98/11830 describe a method and apparatus for hemostasis which greatly simplifies hemostasis and thus greatly reduces patient discomfort following arterial catheterization. The prior art referenced in Applicant's Published PCT Patent application WO 98/11830 and U.S. Pat. No. 5,728,134 is considered to represent the state of the art.

SUMMARY OF THE INVENTION

The present invention seeks to provide improved systems and methodologies for post-catheterization closure.

There is thus provided in accordance with a preferred embodiment of the present invention an apparatus for hemostasis of an artery having a puncture after arterial catheterization. The apparatus includes a catheter introducer having a forward end and a hemostasis device including an elongate flexible hollow shaft having an inflatable anchor balloon at a forward end thereof and an inflatable peripheral balloon adjacent the forward end of the flexible hollow shaft, the hemostasis device is arranged to be insertable into an artery via the catheter introducer.

There is provided in accordance with another preferred embodiment of the present invention an apparatus for hemostasis of an artery having a puncture after arterial catheterization. The apparatus is adapted for use with a catheter introducer having a forward end and includes a hemostasis device, an elongate flexible hollow shaft having an inflatable anchor balloon at a forward end thereof and an inflatable peripheral balloon adjacent the forward end of the flexible hollow shaft, the hemostasis device is arranged to be insertable into an artery via the catheter introducer.

Further in accordance with a preferred embodiment of the present invention the flexible hollow shaft includes a central bore.

Preferably, the flexible hollow shaft includes a wall having an asymmetric cross section, with a relatively thick cross sectional region and a relatively thin cross-sectional region. Typically, there is formed in the relatively thick cross sectional region, a peripheral bore which extends to a peripheral balloon inflation location exterior of the wall and communicates thereat with an interior of the peripheral balloon.

Still further in accordance with a preferred embodiment of the present invention the central bore extends to an anchor balloon inflation location communicating with an interior of the inflatable anchor balloon.

Additionally in accordance with a preferred embodiment of the present invention the anchor balloon and the central bore are configured such that when the anchor balloon is deflated it can be withdrawn into the central bore at the anchor balloon inflation location. Preferably, the anchor balloon is configured such that when it is inflated, it extends beyond the end of the flexible hollow shaft.

Further in accordance with a preferred embodiment of the present invention the apparatus for hemostasis also includes a rod which is displaceable longitudinally inside and along the central bore. The rod which extends through the flexible hollow shaft and terminates at a first end in a manually engageable handle portion. At a second end, the rod is typically attached to the anchor balloon.

Still further in accordance with a preferred embodiment of the present invention the rod includes a multistrand cable surrounded by a plastic cylindrical seal and is attached at an extreme end thereof to an inner surface of the anchor balloon.

Moreover in accordance with a preferred embodiment of the present invention the apparatus for hemostasis also includes a stopcock and associated conduit, communicating with an interior of a head element to which the flexible hollow shaft is fixed at a rearward end thereof.

Further in accordance with a preferred embodiment of the present invention the interior of the head element communicates with the central bore of the flexible hollow shaft and thus communicates with the interior of the anchor balloon at the anchor balloon inflation location.

Still further in accordance with a preferred embodiment of the present invention, the apparatus for hemostasis also includes a stopcock and associated conduit, communicating with an interior the peripheral bore and thus communicates with the interior of the peripheral balloon.

There is further provided in accordance with a preferred embodiment of the present invention, a method for hemostasis of an artery having a puncture after arterial catheterization, the catheterization using a catheter introducer. The method includes the steps of:

inserting into an artery a catheter introducer having a forward end, following arterial catheterization and removal of a catheter from the catheter introducer, introducing into the artery via the catheter introducer, a hemostasis device, which includes an elongate flexible hollow shaft having an inflatable anchor balloon at a forward end thereof and an inflatable peripheral balloon adjacent the forward end, inflating the inflatable anchor balloon inside the artery, causing the inflatable anchor balloon to assume an inflated state, retracting the hemostasis device relative to the catheter introducer, until the anchor balloon in the inflated state engages the forward end of the catheter introducer, retracting the hemostasis device and the catheter introducer until the anchor balloon in the inflated state sealingly engages an inner wall surface of a wall of the artery about the catheter introducer, thereafter retracting the catheter introducer such that the forward end thereof lies outside the wall of the artery, while the anchor balloon in the inflated state blocks blood flow from the artery, inflating the peripheral balloon adjacent the forward end of the catheter introducer as it lies outside an outer surface of the wall of the artery, thereby causing the peripheral balloon to assume an inflated state, deflating the inflatable anchor balloon, thereafter, withdrawing the forward end of the flexible hollow shaft from the artery, while the peripheral balloon seals a region outside the artery and surrounding an aperture in the artery through which the forward end of the flexible shaft was withdrawn, allowing hemostasis to occur thereat and following hemostasis, deflating of the peripheral balloon and removal of the hemostasis device from the patient.

Further in accordance with a preferred embodiment of the present invention the method also includes injecting a hemostatic agent via the hemostasis device to a location external of the artery.

Still further in accordance with a preferred embodiment of the present invention the step of inflating the peripheral balloon includes:

initially inflating the peripheral balloon and thereafter, further inflating the peripheral balloon sufficiently to cause the forward end of the flexible hollow shaft to be withdrawn completely from the wall of the artery and simultaneously to prevent blood flow from the artery through the artery wall.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figures 1, 1A, 2A, 2B:
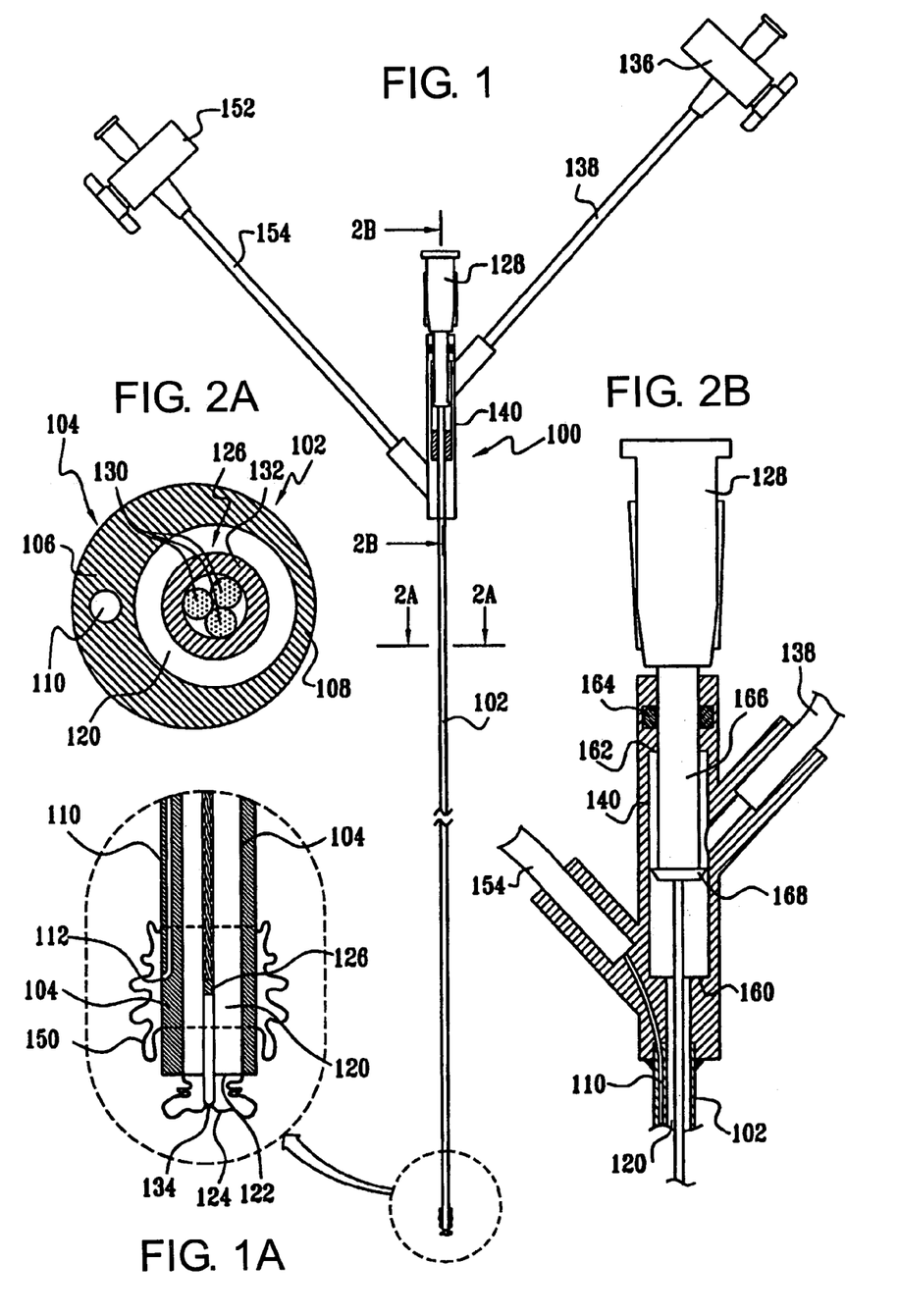
FIG. 1 is a simplified illustration of post catheterization closure apparatus constructed and operative in accordance with a preferred embodiment of the present invention.
FIG. 1A is a close-up of a portion of the apparatus illustrated in FIG. 1.
FIGS. 2A and 2B are sectional illustrations, taken along lines 2A—2A and 2B—2B of FIG. 1.

Reference is now made to FIGS. 1, 2A and 2B, which are simplified illustrations of a hemostasis device 100 for producing hemostasis following arterial catheterization, in accordance with a preferred embodiment of the present invention. The hemostasis device 100 is suitable for insertion via a conventional catheter introducer (not shown) following completion of catheterization and removal of the catheter from the catheter introducer.

In accordance with a preferred embodiment of the present invention hemostasis device 100 comprises a main shaft 102, which preferably has an asymmetric wall 104, typically as shown in FIG. 2A, having a relatively thick region, designated generally by reference numeral 106 and a relatively thin region, designated generally by reference numeral 108. Extending along the wall 104 of the main shaft 102 at the relatively thick region there is preferably formed a bore 110 which extends to an peripheral balloon inflation location 112 exterior of wall 104.

Surrounded by asymmetric wall 104 is a central bore 120 which terminates at an anchor balloon inflation location 122.

Disposed at an end of main shaft 102 at anchor balloon inflation location 122 is an anchor balloon 124. It is a particular feature of the present invention that anchor balloon 124 is able to be withdrawn within bore 120 when deflated and extends beyond the end of main shaft 102 when inflated. Withdrawal of the anchor balloon, when deflated, into the end of central bore 120 adjacent inflation location 122 is preferably assisted by a rod 126 which is displaceable longitudinally inside and along bore 120 and which extends through main shaft 102 and terminates in a manually engageable handle portion 128. Rod 126 preferably comprises a multistrand cable 130 surrounded by a plastic cylindrical seal 132 and is attached at an extreme end thereof, designated by reference numeral 134 to an inner surface of balloon 124.

Anchor balloon 124 is selectably inflated via a stopcock 136 and associated conduit 138, communicating with the interior of a head element 140 to which main shaft 102 is fixed at an end thereof opposite to the end at which balloon 124 is located. The interior of head element 140 communicates with central bore 120 in main shaft 102, which in turn communicates with the interior of the anchor balloon 124 at anchor balloon inflation location 122.

Disposed adjacent the end of bore 110 in communication with peripheral balloon inflation location 112, exterior of wall 104 is a peripheral balloon 150, which is selectably inflated via bore 110, as via a stopcock 152 and associated conduit 154 which communicates with bore 110 via head element 140 as seen in FIG. 1.

It is noted that the head element 140 preferably defines interior travel stop surfaces 160 and 162 as well as an interior seal 164. Interior seal 164 sealingly engages a handle shaft 166 which is fixed to handle portion 128. Handle shaft 166 is preferably formed with a peripheral travel stop engagement protrusion 168 which is adapted to engage stop surfaces 160 and 162 when the handle portion 128 and thus rod 126, fixed thereto, is respectively fully extended or fully retracted.

Reference is now made to FIGS. 3–14A, which illustrate various steps in a preferred mode of operation of the apparatus of FIGS. 1, 2A and 2B FIG. 1.

Figures 3, 3A:
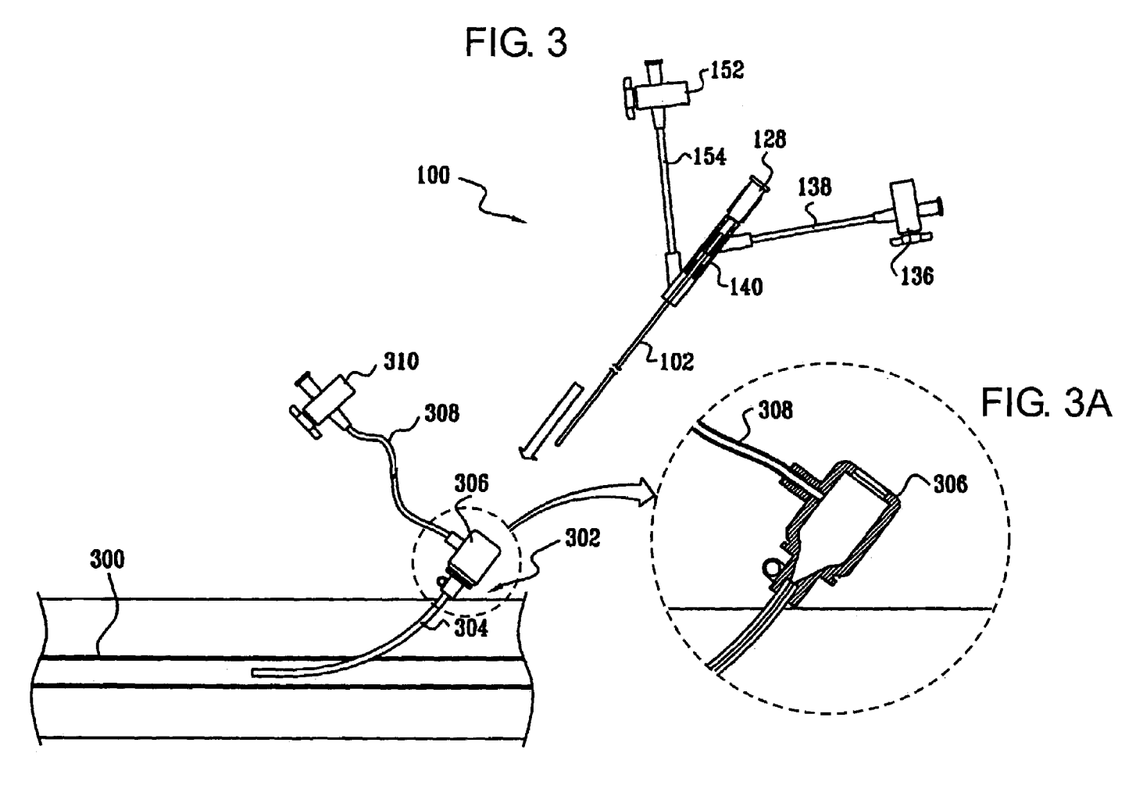
FIG. 3 is a simplified illustration of a stage in a preferred mode of operation of the apparatus of FIG. 1.
FIG. 3A is a close-up of a portion of the apparatus illustrated in FIG. 3.

FIGS. 3 and 3A illustrate the hemostasis device 100 about to be inserted into an artery 300 via a conventional catheter introducer assembly 302, following completion of a catheterization procedure and withdrawal of a catheter (not shown) from the catheter introducer assembly 302. The catheter introducer assembly 302 conventionally includes a sheath 304 and a conventional hemostasis valve 306 to which is coupled a substance introduction conduit 308 having a control valve 310.

Figures 4, 4A, 4B:
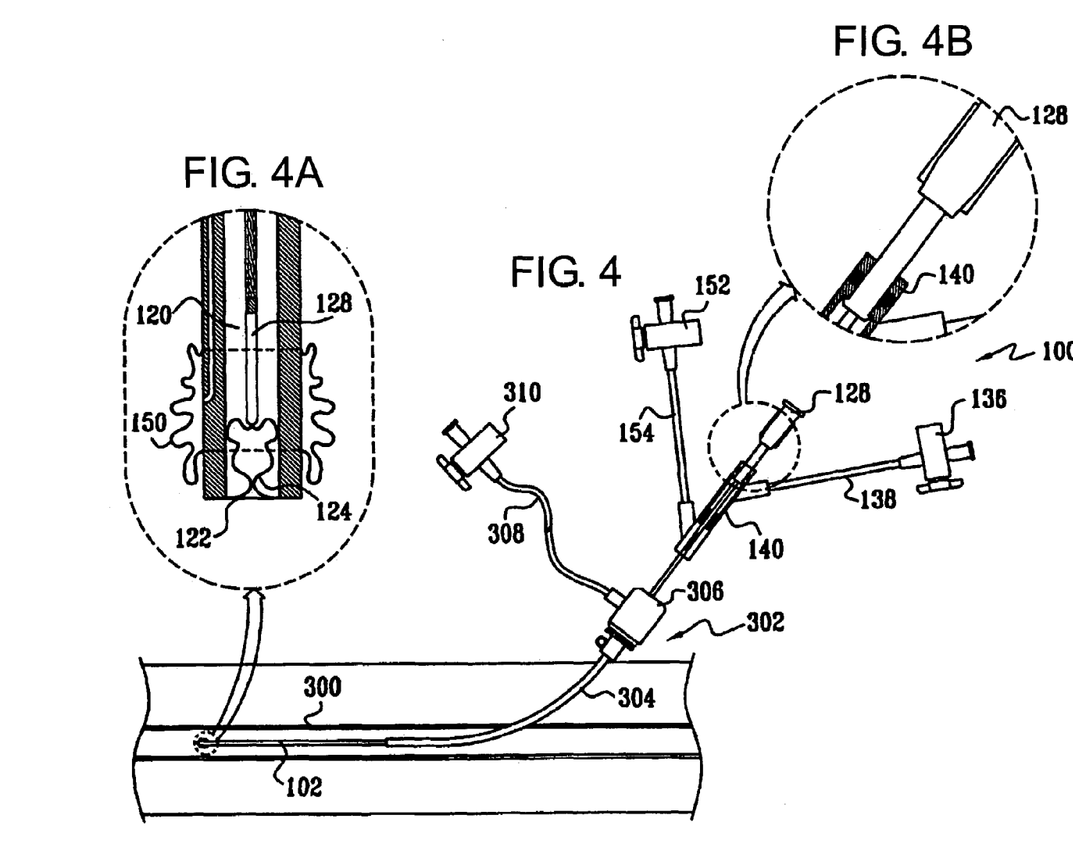
FIG. 4 is a simplified illustration of another stage in a preferred mode of operation of the apparatus of FIG. 1.
FIG. 4A is a close-up of a portion of the apparatus illustrated in FIG. 4.
FIG. 4B is a close-up of another portion of the apparatus illustrated in FIG. 4.

FIGS. 4, 4A, and 4B show the hemostasis device 100 inserted into the catheter introducer assembly 302 such that the outer end of the main shaft 102 extends into the artery 300 well beyond the end of catheter introducer sheath 304. As shown with particularity in FIG. 4, at this stage both anchor balloon 124 and peripheral balloon 150 are deflated, and anchor balloon 124 is preferably fully retracted inside central bore 120 upstream of anchor balloon inflation location 122, by full retraction of handle portion 128 rearwardly of head element 140.

Figures 5, 5A, 5B:
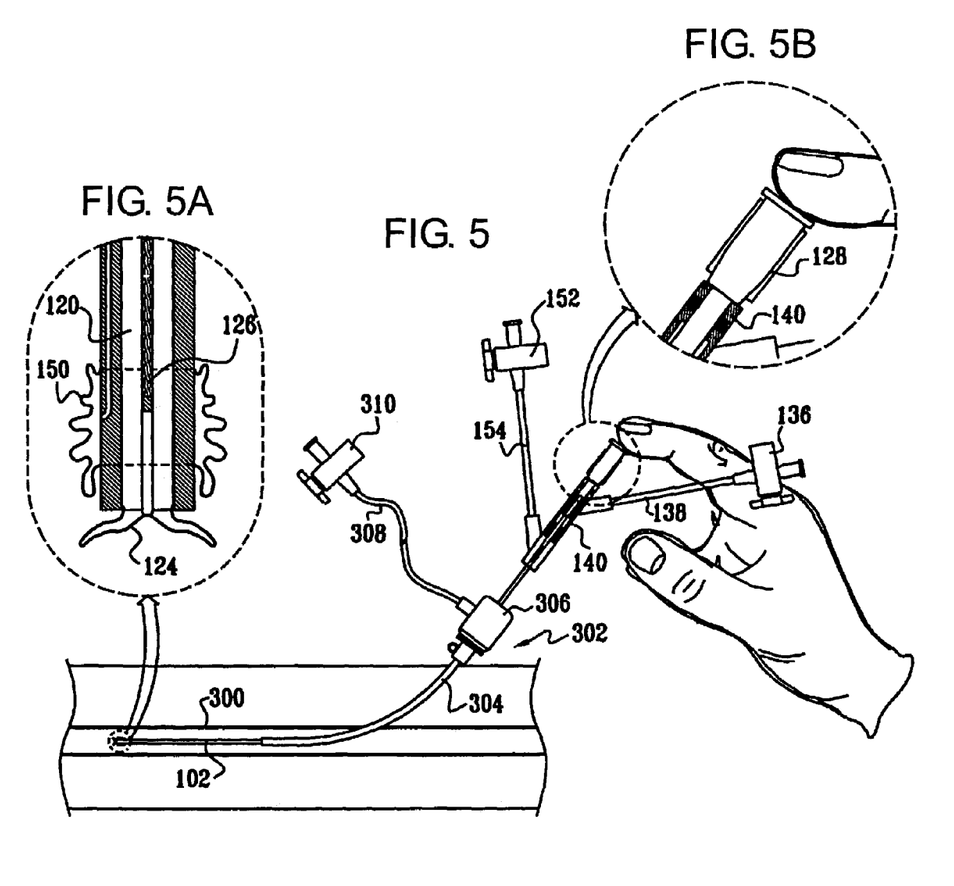
FIG. 5 is a simplified illustration of another stage in a preferred mode of operation of the apparatus of FIG. 1.
FIG. 5A is a close-up of a portion of the apparatus illustrated in FIG. 5.
FIG. 5B is a close-up of another portion of the apparatus illustrated in FIG. 5.

Reference is now made to FIGS. 5, 5A, and 5B, which show initial extension of anchor balloon 124 outside of central bore 120 by extension of handle portion 128 into engagement with head element 140. At this stage, both balloons 124 and 150 remain deflated.

Figures 6, 6A:
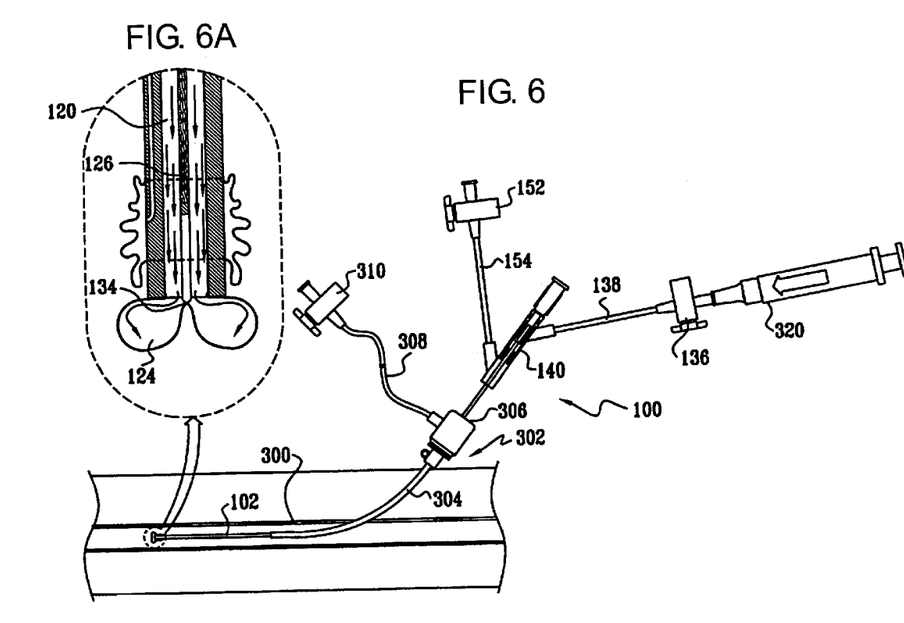
FIG. 6 is a simplified illustration of another stage in a preferred mode of operation of the apparatus of FIG. 1.
FIG. 6A is a close-up of a portion of the apparatus illustrated in FIG. 6.

FIGS. 6 and 6A illustrate initial inflation of the anchor balloon 124, preferably by use of a syringe 320 communicating with central bore 120 via the interior of head element 140, stopcock 136 and associated conduit 138 (FIG. 1). Due to the engagement of extreme end 134 of rod 126 with an inner surface of balloon 124, the inflated balloon preferably has a cusp-type configuration as seen with particularity in FIG. 6.

This cusp-type configuration is associated with a particular feature of the present invention inasmuch as it provides pivotable mounting of the balloon 124 relative to main shaft 102, thereby to enable the anchor balloon 124 to sealingly align itself with the interior wall of artery 300 notwithstanding that the shaft 102 is normally not aligned perpendicularly thereto, as seen in the drawings.

Figures 7, 7A:
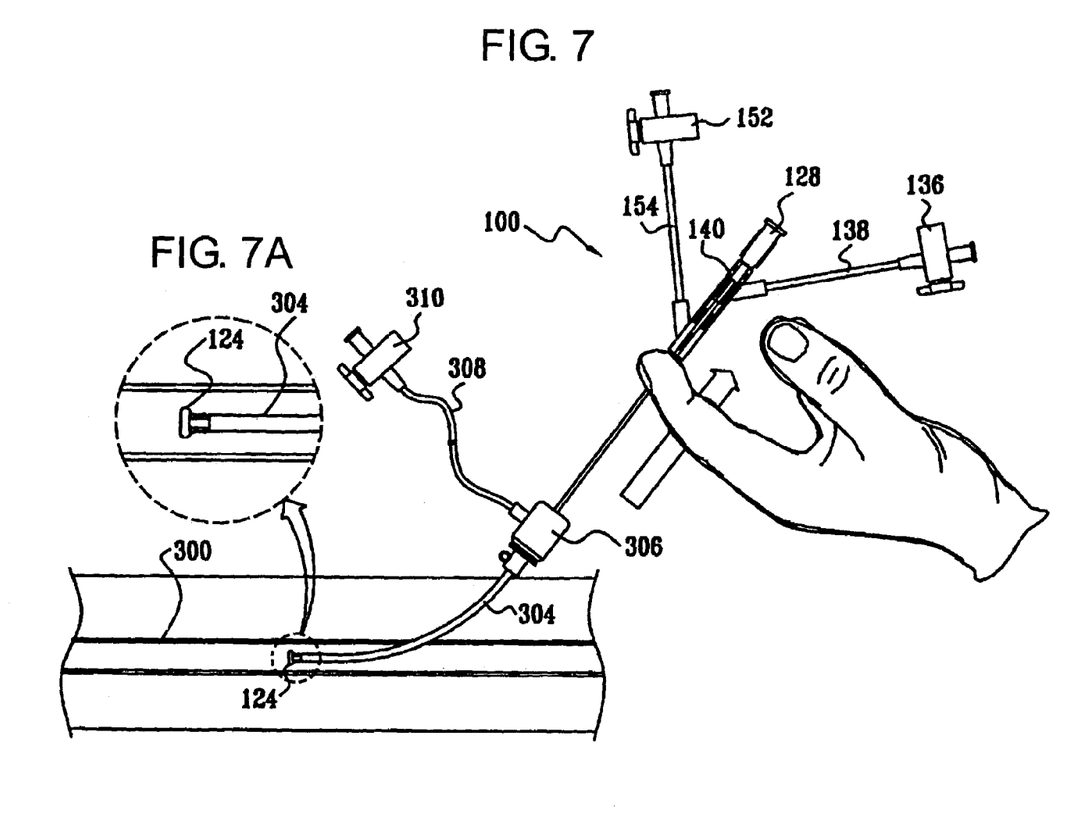
FIG. 7 is a simplified illustration of another stage in a preferred mode of operation of the apparatus of FIG. 1.
FIG. 7A is a close-up of a portion of the apparatus illustrated in FIG. 7.

Following inflation of the anchor balloon 124, the hemostasis device 100 is partially retracted such that the inflated anchor balloon 124 rests tightly against the extreme end of the catheter introducer sheath 304, as seen in FIGS. 7 and 7A.

Figures 8, 8A:
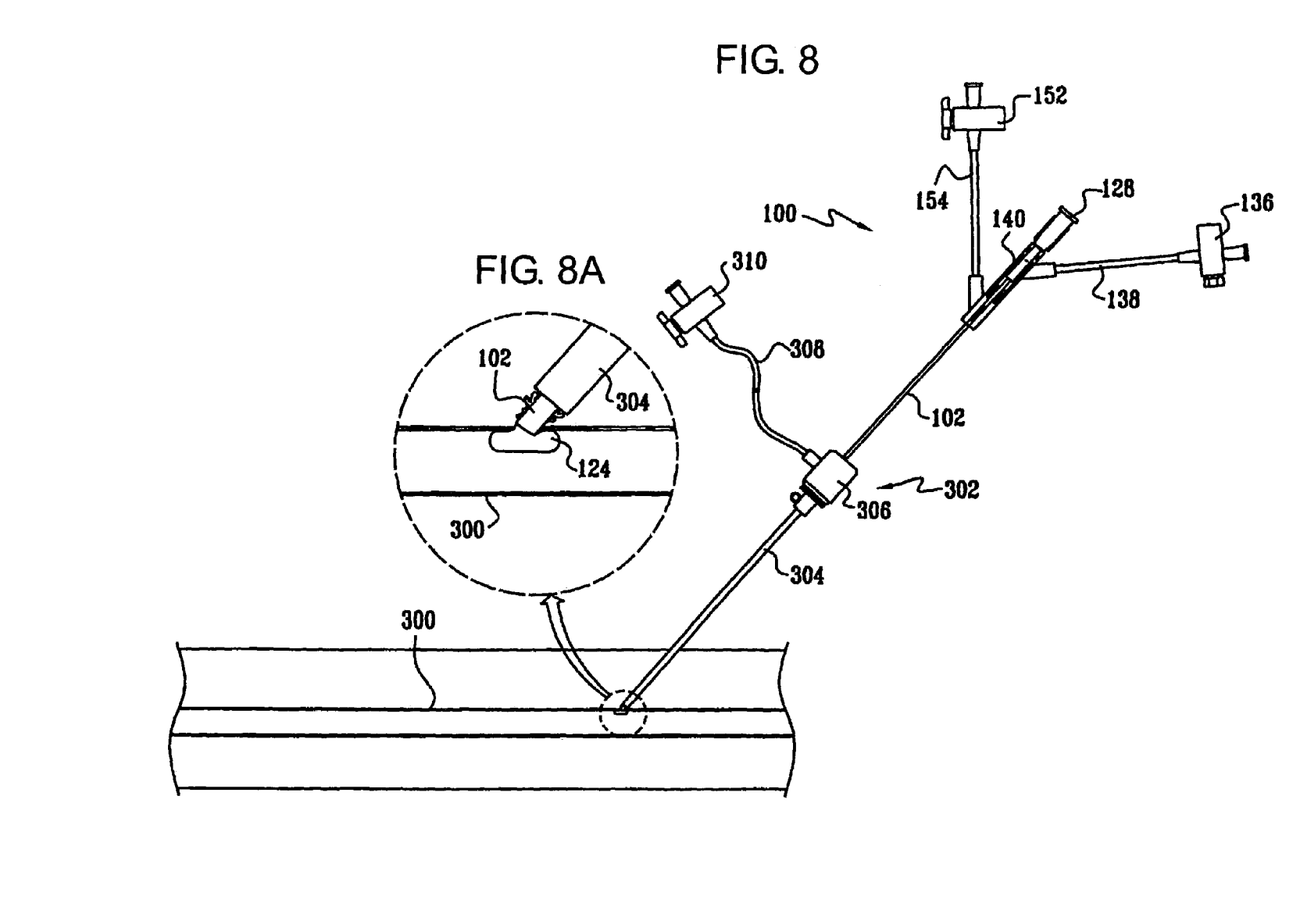
FIG. 8 is a simplified illustration of another stage in a preferred mode of operation of the apparatus of FIG. 1.
FIG. 8A is a close-up of a portion of the apparatus illustrated in FIG. 8.

Thereafter, the catheter introducer assembly 302 and the hemostasis device 100 are withdrawn together, such that the catheter introducer sheath 304 is removed from artery 300 only when the anchor balloon 124 already engages the interior wall of artery 300 in sealing engagement with the aperture in the artery 300 through which the catheter introducer shaft 304 is drawn and through which the main shaft 102 presently extends. This stage is shown in FIGS. 8 and 8A.

Figures 9, 9A:
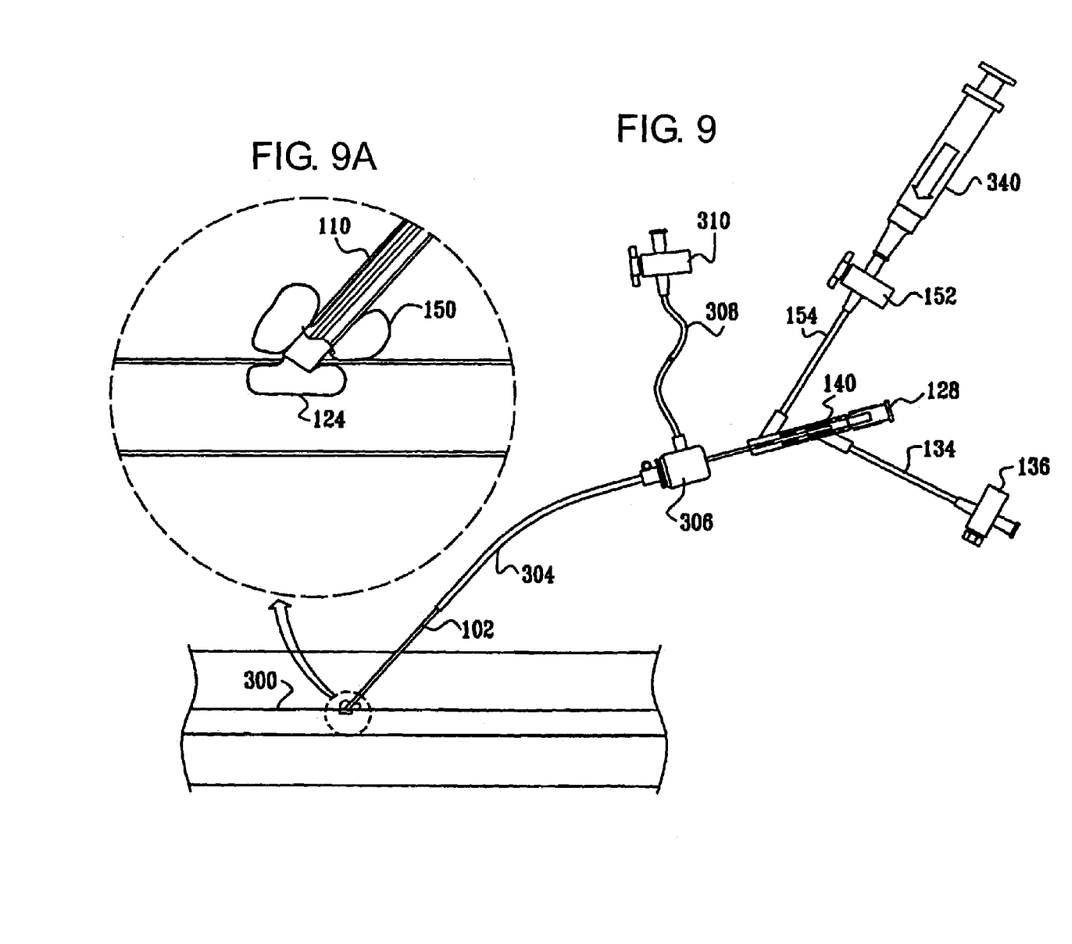
FIG. 9 is a simplified illustration of another stage in a preferred mode of operation of the apparatus of FIG. 1.
FIG. 9A is a close-up of a portion of the apparatus illustrated in FIG. 9.
Figures 10, 10A:
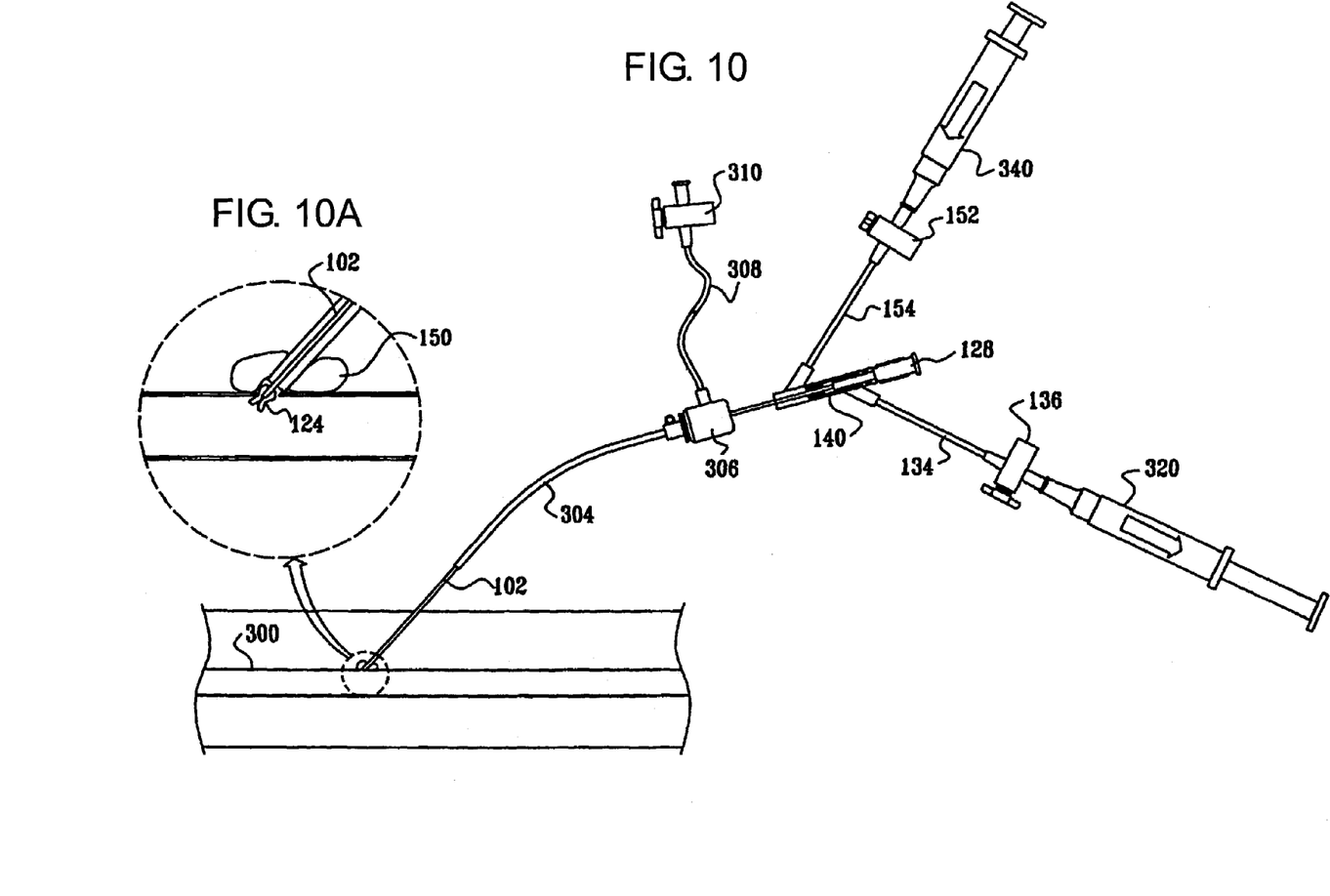
FIG. 10 is a simplified illustration of another stage in a preferred mode of operation of the apparatus of FIG. 1.
FIG. 10A is a close-up of a portion of the apparatus illustrated in FIG. 10.

As seen in FIGS. 9 and 9A, initial inflation of the peripheral balloon 150 is effected, preferably by use of a syringe 340 communicating with bore 110 via head element 140, stopcock 152 and associated conduit 154. Thereafter, as seen in FIGS. 10 and 10A, the anchor balloon 124 is deflated and the peripheral balloon 150 is more fully inflated, which preferably causes the extreme end of the main shaft 102 to be withdrawn from the artery 300 to a location lying just outside the artery wall.

Figures 11, 11A, 11B:
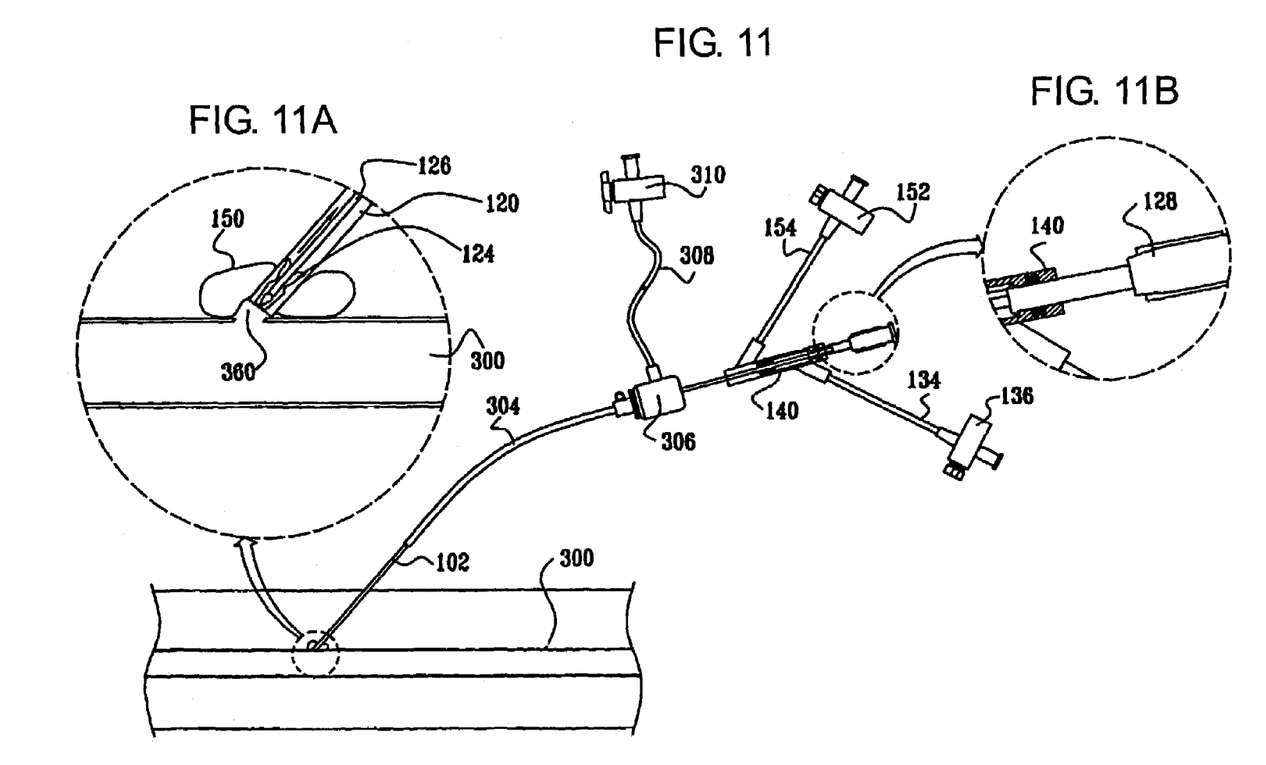
FIG. 11 is a simplified illustration of another stage in a preferred mode of operation of the apparatus of FIG. 1.
FIG. 11A is a close-up of a portion of the apparatus illustrated in FIG. 1.
FIG. 11B is a close-up of another portion of the apparatus illustrated in FIG. 11.
Figures 12, 12A, 12B:
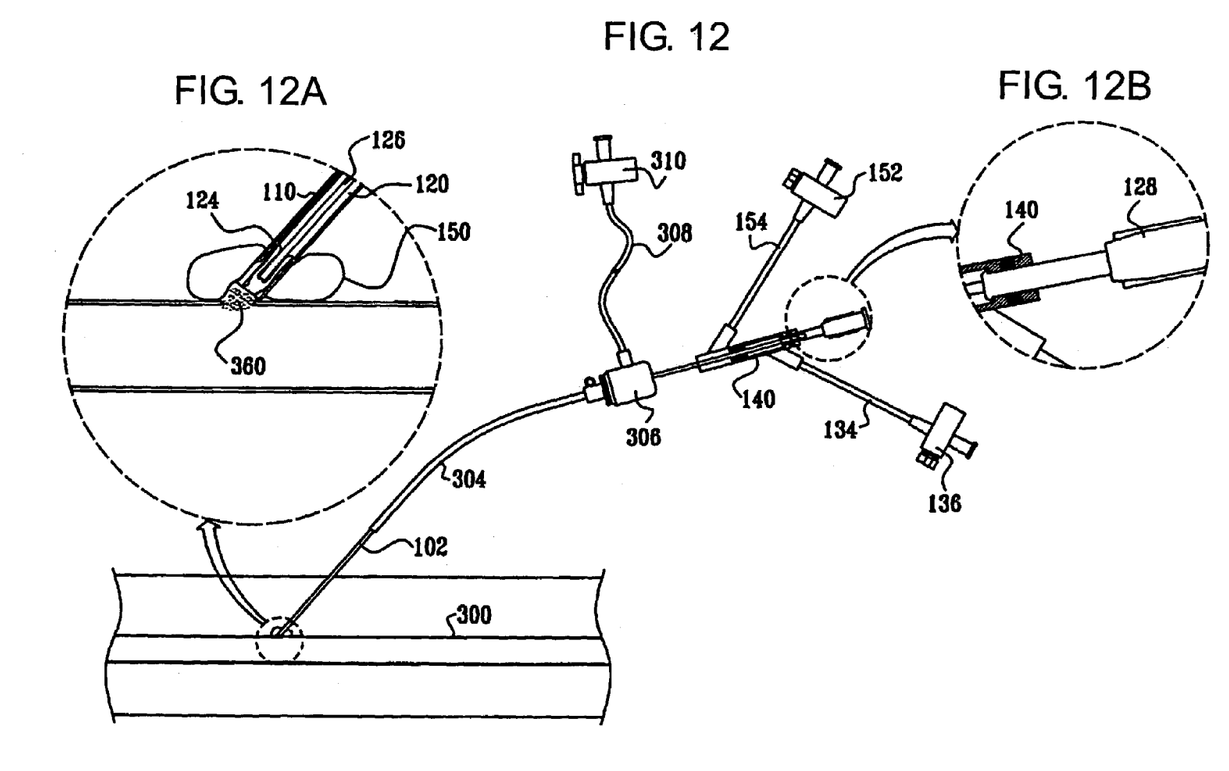
FIG. 12 is a simplified illustration of another stage in a preferred mode of operation of the apparatus of FIG. 1.
FIG. 12A is a close-up of a portion of the apparatus illustrated in FIG. 12.
FIG. 12B is a close-up of another portion of the apparatus illustrated in FIG. 12.

As shown in FIGS. 11, 11A, and 11B the deflated anchor balloon 124 is then retracted within the central bore 120, by full retraction of handle portion 128, allowing for hemostasis to take place in a region 360 outside of artery 300, which region is delimited by inflated peripheral balloon 150, as shown in FIGS. 12, 12A, and 12B.

Figures 13, 13A:
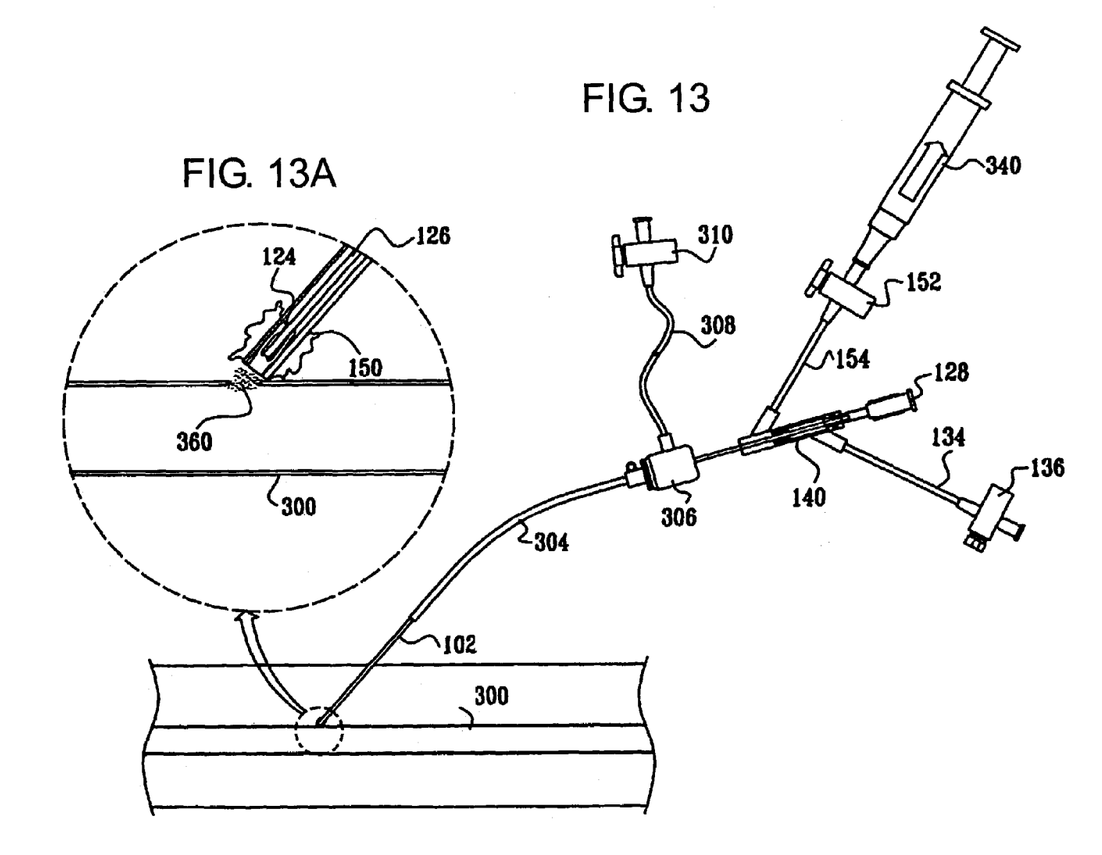
FIG. 13 is a simplified illustration of another stage in a preferred mode of operation of the apparatus of FIG. 1.
FIG. 13A is a close-up of a portion of the apparatus illustrated in FIG. 13.

Once acceptable hemostasis has occurred in region 360, the peripheral balloon 150 is deflated, as shown in FIGS. 13 and 13A, preferably by operation of syringe 340 communicating with bore 110 via head element 140, stopcock 152 and associated conduit 154.

Figure 14:
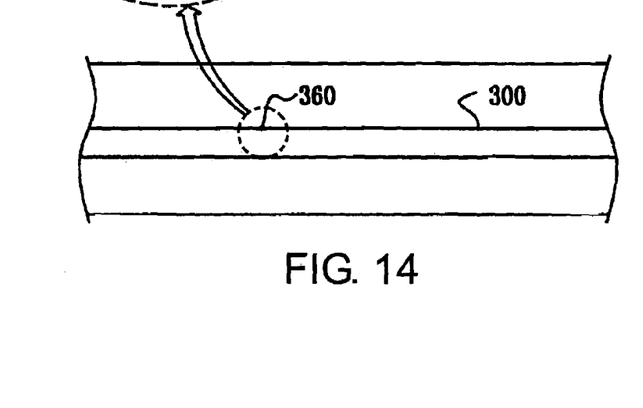
FIG. 14 is a simplified illustration of another stage in a preferred mode of operation of the apparatus of FIG. 1.
Figure 14A:
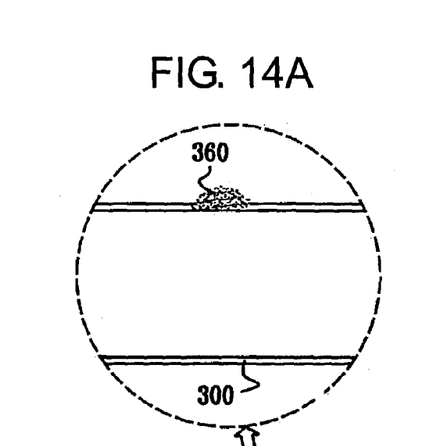
FIG. 14A is a close-up of a portion of the apparatus illustrated in FIG. 14.

Thereafter, the hemostasis device 100 is entirely withdrawn from the patient, leaving a region 360 of hemostasis outside of artery 300, as shown in FIGS. 14 and 14A.

It will be appreciated by persons skilled in the art that the present invention is not limited by what has been particularly shown and described hereinabove. Rather the scope of the present invention includes both combinations and sub-combinations of the various features described hereinabove and shown in the drawings as well as modifications and further developments thereof which would occur to a person of ordinary skill in the art upon reading the foregoing description and which are not in the prior art.

What is claimed is:

1. A method for hemostasis of an artery having a puncture after arterial catheterization, said catheterization using a catheter introducer, the method comprising the steps of:

inserting into an artery a catheter introducer having a forward end;

following arterial catheterization and removal of a catheter from the catheter introducer, introducing into the artery via said catheter introducer, a hemostasis device including an elongate flexible hollow shaft having an inflatable anchor balloon at a forward end thereof and an inflatable peripheral balloon adjacent said forward end of said hollow shaft;

inflating the inflatable anchor balloon inside the artery, causing said inflatable anchor balloon to assume an inflated state having a cusp-type configuration;

retracting said hemostasis device and said catheter introducer until said anchor balloon in said inflated state engages an inner wall surface of a wall of the artery about said catheter introducer;

thereafter retracting said catheter introducer such that the forward end thereof lies outside the wall of the artery, while said anchor balloon in said inflated state blocks blood flow from the artery;

inflating said peripheral balloon as it lies outside an outer surface of the wall of the artery, thereby causing the peripheral balloon to assume an inflated state;

deflating the inflatable anchor balloon;
thereafter, while said peripheral balloon seals a region outside said artery and surrounding an aperture in said artery, allowing hemostasis to occur thereat; and
following hemostasis, deflating said peripheral balloon and removing said hemostasis device from the patient.

2. A method according to claim 1 and also comprising injecting a hemostatic agent via the hemostasis device to a location external of the artery.

3. A method according to claim 1 and wherein said inflating said peripheral balloon includes:
initially inflating said peripheral balloon; and
thereafter, further inflating said peripheral balloon sufficiently to cause said forward end of said flexible hollow shaft to be withdrawn completely from the wall of the artery and simultaneously to prevent blood flow from the artery through the artery wall.

* * * * *